US006864100B1

(12) United States Patent
Ribbe et al.

(10) Patent No.: US 6,864,100 B1
(45) Date of Patent: Mar. 8, 2005

(54) AUTOMATED PROTEIN PURIFICATION THE MULTIWELL FORMAT BY VACUUM FILTRATION

(75) Inventors: Joachim Ribbe, Düsseldorf (DE); Frank Schäfer, Düsseldorf (DE); Kerstin Steinert, Langenfeld (DE); Helge Lubenow, Solingen (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 10/049,003

(22) PCT Filed: Aug. 2, 2000

(86) PCT No.: PCT/EP00/07478

§ 371 (c)(1),
(2), (4) Date: Feb. 4, 2002

(87) PCT Pub. No.: WO01/10886

PCT Pub. Date: Feb. 15, 2001

(30) Foreign Application Priority Data

Aug. 6, 1999 (DE) .......................................... 199 37 187

(51) Int. Cl.[7] ................................................ G01N 1/34
(52) U.S. Cl. ........................... 436/178; 436/86; 436/94; 436/161; 436/177; 422/61; 422/70; 422/101
(58) Field of Search ................................. 436/161, 175, 436/177, 178, 86, 94; 422/101, 61, 70, 102; 435/288.4, 288.5, 288.6, 297.1, 297.5, 305.2, 306.1

(56) References Cited

U.S. PATENT DOCUMENTS

| 4,364,263 | A | * | 12/1982 | Sankoorikal et al. ...... 73/61.56 |
| 4,948,442 | A | * | 8/1990 | Manns ....................... 156/73.1 |
| 5,112,488 | A | * | 5/1992 | Lemonnier ................... 210/541 |
| 5,296,358 | A | * | 3/1994 | Battistel et al. ................ 435/49 |
| 5,695,639 | A | * | 12/1997 | Johnson ....................... 210/474 |
| 6,277,648 | B1 | * | 8/2001 | Colpan ....................... 436/177 |
| 6,464,942 | B2 | * | 10/2002 | Coffman et al. ............. 422/100 |

FOREIGN PATENT DOCUMENTS

| DE | 423 00 89 | 3/1994 |
| EP | 0 249 932 | 12/1987 |
| EP | 0 376 080 | 7/1990 |
| EP | 0 616 638 | 9/1994 |

OTHER PUBLICATIONS

Bell et al., *Life Science News*, 1: 1–3 (1998).
Felleisen et al., *Biotechniques*, 20: 616–620 (1996).

* cited by examiner

*Primary Examiner*—Jan M. Ludlow
(74) *Attorney, Agent, or Firm*—Yankwich & Associates; Leon R. Yankwich; David G. O'Brien (57) ABSTRACT

The invention relates to a process and a reagent kit for obtaining clear solutions containing cell contents from biological samples in a high throughput process, comprising the steps of preparing a plurality of protein-containing solutions which contain insoluble ingredients, in separate chambers of a multi-chamber filtration unit, eliminating insoluble ingredients by filtering the solutions through the multi-chamber filtration unit with the application of a pressure differential, while preventing cross contamination between adjacent chambers by chemical and/or mechanical means, and collecting the individual filtrates separately in collecting containers, as well as a process for recovering cell contents from the clear solutions obtained. The invention further relates to the use of an apparatus for recovering clear protein-containing solutions from biological samples.

31 Claims, 3 Drawing Sheets

FIG. 1

Automatic purification of chloramphenicol acetyl transferase (CAT) by anion exchange chromatography (matrix suspension) in a 96 well format.

FIG. 2

Automatic purification free from cross contamination.

FIG. 3A

Automatic purification without taking measures to prevent cross contamination.

FIG. 3B

AUTOMATED PROTEIN PURIFICATION THE MULTIWELL FORMAT BY VACUUM FILTRATION

The present invention relates to a process and a reagent kit for obtaining clear solutions containing cell contents from biological samples in a high throughput method and for recovering cell contents from the clear solutions obtained. The invention further relates to the use of an automated apparatus for recovering clear solutions containing proteins.

In the field of biochemistry and molecular biology there is frequently a need, particularly in screening, to examine a number of biological samples more closely in order to identify desired clones, for example, or determine the presence or content of cell contents in biological samples. To reduce the time taken and hence the costs and the possibility of errors, methods or systems have been developed in the past to simplify the procedure. One approach with a view to reducing the workload consisted in providing systems which make it possible to work on a plurality of samples in parallel, such as microtitre plates, for example, multiple pipettes suitable for this purpose or rotor inserts capable of holding microtitre plates. A further approach sets out to automate individual steps of the process as far as possible, e.g. by using suitable robots.

Felleisen et al (Biotechniques 20, 616–620 (1996), describe a process for purifying recombinant Maltose-Binding-Protein (MBP) fusion proteins a 96-well format. The process starts with clear cell lysates prepared in the conventional manner and placed in the wells of a 96-well plate, binding the MBP fusion proteins contained in the supernatant to maltose-coated surfaces and eluting the MBP fusion proteins by the addition of excess maltose or denaturing reagents. A disadvantage of this process is that it is not automated and cannot be automated because of the preparation of clear cell lysates by centrifugation. The process can only be used under native conditions but not under denaturing conditions and produces a low yield (about 2 µg per well).

Bell et al (http://www.apbiotech.com/publications/LSN-1-5/gst-micro.htm, 1999) describe a process for the parallel purification of up to 24 recombinant glutathione-S-transferase (GST) fusion proteins. Clear cell lysates are prepared by centrifugation and added to separate microchromatography columns. The binding and washing steps that follow are performed by centrifugation or by applying a vacuum. Elution is carried out by the addition of reduced glutathione to individual microreaction vessels. A disadvantage of this process is that it is not automated and cannot be automated because of the preparation of clear cell lysates by centrifugation. The process can only be carried out under native conditions and allows only 24 samples to be worked on in parallel. In addition, there is a high risk of confusion owing to the use of individual reaction vessels.

Sheer and Pitt (High Throughput Sample Preparation of Proteins and Peptides for Structural Characterization, Poster Nr.446-0T, 13–15 Jul. 1997, 11th Symposium of the Protein Society, Boston, Mass.) describe a process for charging the 96 wells of a 96-well microtitre plate with dry powdered chromatography material using a "multiscreen column loader". After the swelling and equilibration of the material 96 batches can be chromatographically processed in parallel, all the steps being done by centrifugation. This process applies only to chromatographic purification but not to the preparation of samples.

The documents mentioned above describe the purification of proteins in parallel batches but are not all automated and cannot be automated in the form described. The starting material used is clear cell lysates in each case, which have been produced in the conventional manner, e.g. by centrifugation of the individual samples and removal of the supernatants. This involves the need for numerous handling steps and consequently is highly time-consuming and brings a risk of samples being mixed up.

DE 4230089 describes a laboratory robot for the fully automatic working up of up to 30 synthetic peptides from solid phase synthesis. There is no disclosure of the working up of biological material such as cells or cell extracts, for example.

EP-A-0376080 describes a process for extracting and purifying DNA without any centrifugation steps. There is no disclosure of the parallel working up of a number of samples, particularly in a high throughput process.

EP-A-0249932 describes an automated process for purifying physiologically active substances on a process scale. The process is based on the separation of cells or cell components by macrofiltration, ultrafiltration to separate substances having a lower molecular weight than the substance which is to be isolated, and a step of affinity chromatography. There is no disclosure of the parallel purification of substances, particularly by a high throughput process.

The above European patent applications describe processes capable of automation for purifying DNA or proteins from cells or cell suspensions. However, they disclose only processes for purifying these substances from an individual sample and not in a high throughput process and accordingly they do not take account of the particular circumstances which arise in high throughput applications.

Because of the small spacing between the separate samples there is a considerable problem in high throughput applications in cross-contamination by solutions from adjacent wells or chambers. This risk is present particularly in filtration steps using a multi-chamber filtration unit, particularly if the solution to be filtered tends to foam vigorously. This problem is particularly serious in the production of clear lysates from cell cultures. For this reason, known parallel processes start with clear cell lysates which have been obtained in conventional manner, i.e. by centrifugation, cf. the prior art mentioned above.

The problem on which the present invention is based was thus to provide a simple and rapid process for obtaining clear solutions from biological samples, particularly from cells or cell suspensions or crude lysates, in parallel.

In one aspect the invention thus relates to a process for obtaining clear solutions containing cell contents from biological samples in a high throughput process, comprising the steps of:

(a) preparing protein-containing solutions which contain insoluble ingredients, in separate chambers of a multi-chamber filtration unit, (b) removing insoluble components by filtering the solutions through the multi-chamber filtration unit by applying a differential pressure, cross contamination between adjacent chambers being prevented by chemical and/or mechanical means, and (c) collecting the individual filtrates separately in collecting containers.

For the purposes of this application the phrase biological sample denotes a sample which contains biological material. The biological material originates, for example, from all kinds of tissues, bone marrow, human and animal body fluids such as blood, serum, plasma, urine, sperm, cerebrospinal fluid, sputum and smears, plants, parts of plants and plant extracts, e.g. juices, fungi, microorganisms such as bacteria or viruses, pro- and/or eukaryotic cells or cell cultures, fossilised or mummified samples, soil samples, clarified sludge, sewage and foods. In particular, the biological sample may contain recombinant material, e.g. eukaryotic and/or prokaryotic cells modified by recombinant techniques.

The protein-containing solution contains peptides and/or polypeptides from the biological material in soluble form. For example, these soluble peptides and/or polypeptides are secreted substances which are present in the biological sample and/or are secreted by cells in the biological sample. Alternatively, they may be peptides and/or polypeptides which occur inside cells or are expressed recombinantly and have been released by the breakup of cells. In one particular embodiment the protein-containing starting solutions (i.e. solutions which contain insoluble ingredients) are crude cell lysates, the lysis being carried out under protein-solubilising conditions. Moreover, the protein-containing starting solutions may also be fractions of crude cell lysates. One way of obtaining a lysate fraction is, for example, to carry out the lysis under protein-precipitating conditions and to separate the nucleic acids and to take up the residue again under protein-solubilising conditions.

The expressions "clear solution" and "filtrate" are used synonymously here and refer to a solution which is substantially free from insoluble matter such as cell debris for example.

The solutions will generally be of different origins, but it is also possible to conceive of applications in which aliquots of an identical sample are processed in parallel.

The term "high throughput" here denotes the parallel processing of at least 24, preferably at least 48 and most preferably 96 samples or more, e.g. 384 samples.

According to one embodiment, cross-contamination is avoided by reducing foaming. Such foaming occurs during the filtering of a protein-containing solution at the exit from the individual chambers of a multi-chamber filtration unit. The head of foam which forms may merge with the foam at adjoining chamber outlets and lead to cross contamination. Foaming is observed during the filtration of lysates with a protein concentration of $\geq 0.1$ mg, per ml of lysate. Foaming is also observed in the filtration of (complex) culture media which contain proteins. Such culture media are known to the experts and contain for example extracts of yeast cells (e.g. LB, TB, dYT and YP media), partially digested extracts of animal and plant tissue (e.g. tryptones, peptones, soya peptone), hydrolysates of e.g. casein, lactalbumin or gelatin or blood serum constituents, or they may be protein-enriched serum-free media (e.g. CHO-S-SFMII). Vigorous foaming occurs with protein contents of $\geq 0.01$ mg per ml of medium.

In a preferred embodiment of the invention the foaming is reduced by adding an antifoam to the protein-containing solutions, particularly by covering the protein-containing solutions with antifoam. Suitable antifoams include, for example, primary, secondary or tertiary alcohols, particularly $C_{1-6}$ alcohols, antifoams based on silicon oil or emulsions thereof such as for example Antifoam A (SIGMA), Wacker silicon antifoam emulsion SRE (antifoam reagent DX, Wacker) or Dow Corning antifoam MSA compound (Dow Corning), non-silicone organic antifoams or emulsions thereof, e.g. Antifoam 204 (SIGMA), plant-based antifoams, particularly alkoxylated fatty acid esters, e.g. Structol J673 (Schill and Sailacher), long-chained alkanes ($C_6$ and longer), mineral oils, polyglycols such as polypropylene glycols and polyethylene glycols, and mixtures thereof, e.g. mixtures which contain silicone and non-silicone antifoams, e.g. Antifoam 289 (SIGMA). Preferably, the antifoam is an alcohol, particularly ethanol or isopropanol.

The concentration of antifoam varies depending on the type of antifoam substance, for example alcohols, especially ethanol, are used in concentrated form whereas antifoams based on silicon oil are used in a concentration of around 0.1%.

If the antifoam is added by pouring it on top, as in the preferred embodiment, the volume of antifoam required will depend on the diameter of the chambers or the column of liquid of antifoam, i.e. it is largely independent of the volume of the protein-containing solutions. Moreover, the volume is also dependent on the type of antifoam. Using ethanol as antifoam it was found that a column height in the range from 0.05 cm to 1 cm, preferably 0.1 cm to 0.3 cm and particularly about 0.2 cm gave good results (based on a chamber diameter of 0.8 cm; if the diameter of the chambers is altered, adjustments may be required to the height of the column).

According to another embodiment of the invention cross-contamination is prevented by the use of a multi-chamber transfer unit between the outlet end of the multi-chamber filtration unit and the inlet end of the collecting containers. By "multi-chamber transfer unit" is meant a unit having separate passages, the inlet openings of which correspond to the outlet openings of the individual chambers of the multi-chamber filtration unit and the outlet openings of which correspond to the inlet openings of the collecting containers. At the inlet end the transfer unit fits in substantially sealed manner against the outlet openings of the multi-chamber filtration unit to prevent cross-contamination by foaming. At the outlet end a non-sealing fit on the inlet openings of the collecting containers may be provided in order to allow a pressure differential to be applied between the inlet and outlet ends of the multi-chamber filtration unit. Alternatively, at the outlet end of the multi-chamber filtration unit, a tight seal may be provided with the inlet end of the collecting containers in order to allow a pressure differential to be applied between the inlet end of the multi-chamber filtration unit and a possible outlet end of the collecting containers. If the collecting containers contain a chromatography matrix, filtration of the starting solutions and further processing, such as for example binding the cell contents which are to be purified to the matrix may be carried out in a vacuum step (see below). The transfer unit consists, for example, of a sealing mat, an aluminium, glass or plastics block provided with through-bores or an arrangement of corresponding tubes or hoses.

In one particular embodiment the process according to the invention starts with crude cell lysates which are prepared in separate chambers of a multi-chamber filtration unit. The cell lysates may have previously been prepared by mixing cells or cell suspensions with lysing reagents, or the lysis may be carried out directly in the individual chambers of the multi-chamber filtration unit by the addition of cells and lysing substances and optionally incubation. The lysis is carried out under protein-solubilising conditions or comprises a solubilising step for proteins after the separation of one or more fractions.

The protein-containing solutions are separated from the insoluble ingredients by applying a pressure differential between the inlet end and outlet end of the multi-chamber filtration unit, a lower pressure prevailing at the outlet end. The pressure differential can be produced by applying overpressure at the inlet end or preferably a vacuum at the outlet end.

The filter present in the separate chambers of the multi-chamber filtration unit is preferably a filter the pore size of which decreases in the direction of flow of the filtrates through the filter. A filter of this kind is described in EP 0616638 B1, to which reference may be made for further details. It combines the advantages of a coarse filter (minimal blockage of the filter pores) with those of a close-mesh filter (good retention of fine insoluble ingredients). However, a conventional filter with a uniform pore size is also suitable.

After the filtration step the filtrates are collected separately in collecting containers, expediently in the separate chambers of a multi-chamber unit. In particular, if the intention is to process the clear solutions further (see below) this multi-chamber unit is generally a further filtration or chromatography unit.

In one particular embodiment the process according to the invention also includes recovering cell contents from filtrates obtained in this way. For this purpose the process comprises, for example, one or more additional filtration steps, e.g. ultrafiltration, which separates off substances having a lower molecular weight than the cell contents being sought, and concentration to reduce the volume of the sample.

In order to recover cell contents, the process preferably comprises at least one chromatographic separation step and/or precipitation step. A precipitation step comprises, for example, the addition of ethanol in a sufficient concentration to precipitate nucleic acids or the addition of ether in a sufficient concentration to precipitate peptides. A chromatographic separation step comprises binding the desired cell contents to a suitable chromatographic material, removing the supernatants and then eluting the contents.

The chromatographic material is not subject to any particular restrictions and can be selected to suit the particular cell contents which are being separated. For example, the chromatographic material may be an ion exchange matrix.

Suitable matrix materials include for example agarose, silica, nitrocellulose, cellulose, acrylamide, latex, polystyrene, polyacrylate, polymethacrylate, polyethylene polymers such as polyvinyl alcohol, glass particles, silicates such as calcium, magnesium and aluminium silicates, metal oxides such as titanium oxides, apatites and combinations thereof. Preferred matrix materials are silica gel and/or agarose.

In another preferred embodiment the process according to the invention for recovering cell contents comprises a step of chromatographic separation by means of an affinity matrix. Affinity matrices of this kind are known in the art and comprise for example the ligand systems listed below (coupled to a matrix material, see above).

| affinity ligand | molecule to be isolated therewith |
| --- | --- |
| antigen | specific antibody |
| antibody | specific antigen |
| antibody | specific antibody |
| antibody (e.g. anti-human IgG, anti-mouse IgG) | specific category of antibodies such as IgG molecules from humans or mice |
| protein A or protein G | specific categories of antibodies |
| streptavidine or streptavidine-labelled fusion proteins | biotin, avidine, biotin- or avidine-labelled fusion proteins |
| glutathione | glutathione-S-transferase (GST) or GST fusion proteins |
| cellulose | cellulose-binding domains (CBD) or CBD fusion proteins |
| calmodulin | calmodulin-binding protein (CBP) or CBP fusion proteins |
| amylose | maltose-binding proteins (MBP) or MBP fusion proteins |
| ion exchanger groups | biomolecules |
| ligand for hydrophobic interactions | biomolecules |
| oligo dT | polyA regions, e.g. of mRNA molecules |
| nucleic acids | hybridising nucleic acid |
| nucleic acids, defined sequence | specifically nucleic acid-binding biomolecules, e.g. proteins |
| protein | interaction partners (protein, nucleic acids in general, nucleic acids of a particular sequence, small biomolecules) |
| small biomolecules | proteins, nucleic acids |
| cell-binding ligands, e.g. polypeptide | cells via the binding of cell surface molecules |
| phage-binding ligands, e.g. polypeptide | phages via the binding of molecules to the phage surface |
| antibodies | cells or phages via the binding of surface molecules |

Another example of affinity matrices is a metal chelate affinity matrix for purifying proteins or peptides. Using an Ni-NTA matrix (obtainable from Qiagen) outstanding results were obtained in the purification of 6×His-labelled proteins (see the Examples).

The form of the matrix material is not particularly restricted; materials in the form of suspensions or membrane may be used. Examples include, in each case functionalised, membranes, (monodispersed) latex beads, continuous bed material, polymer chromatography media, silica particles, etc. By "functionalised" is meant the presence of a group capable of entering into an affinity interaction with the desired cell contents. One specific example of a chromatographic medium of the suspension type is Ni-NTA superflow (obtainable from Qiagen).

The process according to the invention for obtaining cell contents appropriately comprises one or more washing steps. The separation of liquids, i.e. the supernatant after precipitation or binding of the desired cell contents to a chromatographic material, and the washing liquid is preferably carried out according to the invention by applying a pressure differential, particularly an underpressure at the outlet end. If necessary, suitable measures are taken in these additional filtration and/or chromatography steps to prevent contamination by liquids in adjacent chambers, for example by the addition of an antifoam or by using a transfer unit.

In one particular embodiment the liquids which are to be discarded (washing liquids etc.) are eliminated using a drainage unit. This drainage unit corresponds at the inlet end to the multichamber transfer unit described above, i.e. the supernatants are taken away through separate passages from the outlet end of a multichamber filtration unit. At the outlet end these liquids are conveyed through the drainage unit into a waste collection tank.

After the process for recovering or purifying/isolating cell contents has been carried out the solutions which contain the cell contents are collected separately in collecting containers, particularly in the separate chambers of a multichamber unit.

The process according to the invention may also comprise steps for analysing and/or preserving the cell contents. Analysis steps generally comprise taking an aliquot, for example, and placing it in an electrophoresis unit, e.g. SDS-PAGE and/or a spectroscopy unit, e.g. a mass spectrometer or an assay. A specific example of a preservation step is freeze-drying.

The process according to the invention is suitable for recovering a plurality of cell contents, particularly for obtaining peptides, polypeptides, nucleic acids and/or metabolites. The prerequisite is a suitable procedure for separating the cell contents from other substances using one or more filtration, precipitation and/or chromatographic separation steps. Preferably, the process is used to obtain peptides or polypeptides, with polypeptides generally containing at least 50 amino acids.

The polypeptides include for example proteins, glycoproteins and lipoproteins which are optionally made up of a number of subunits and/or contain prosthetic groups such as antibodies or enzymes. Moreover, by suitably combining the process steps, it is possible to recover a plurality of cell contents from the same lysate. For example, using a complex of process steps, peptides or polypeptides can be isolated by binding to an affinity matrix and in another complex nucleic acids, e.g. plasmid DNA coding for these peptides or polypeptides, may be recovered.

The process according to the invention is intended particularly for the fast parallel processing of samples on a laboratory scale, i.e. for a capacity of up to 50 ml, preferably up to 20 ml and most preferably 0.1 to 2 ml in each chamber of the multichamber filtration unit in which the protein-containing starting solutions are provided.

Other advantages of the process according to the invention, apart from avoiding cross contamination in a high throughput process, include in particular:

- a high automation of the parallel preparation of clear cell lysates,
- the avoidance of manual transfer steps and/or pipetting steps,
- a high automation of recovery of cell contents from crude cell lysates,
- high yields with a high level of purity of the cell contents obtained,
- theoretical possibility of applying the process both under native and under denaturing conditions,
- reducing the sources of error by automating the process and using multichamber units,
- the speed of the process,
- the flexibility of the system.

The process according to the invention is suitable for recovering clear protein-containing solutions or for removing cell contents from a biological sample, e.g. prokaryotes such as for example *E. coli*, eukaryotes such as e.g. *Saccharomyces cerevisiae*, plant, animal and human tissue and culture cells, insect cells, fungi, Archaea etc and for automated phage display assays, for example.

Practical applications for the high throughput process according to the invention (HT=high throughput) consist, for example, of:

Functional Genomics:
- HT characterisation of genes/open reading frames at the protein level within the context of genome sequencing projects (e.g. yeast genome project, human genome project)

Functional Proteomics:
- HT purification of recombinant proteins and of protein and peptide complexes;
- HT purification of recombinant proteins and of protein and peptide complexes as a sample preparation for immobilising on surfaces (e.g. microtitre plates, microreactors, protein chips [microarrays]);
- HT purification of recombinant proteins as sample preparation for active substance screening programs;
- HT purification of recombinant proteins and of protein and peptide complexes as sample preparation for studies of interaction, e.g. within the context of cell measurement proteomics projects;
- isolation of peptides, proteins, peptide or protein complexes and other biomolecules (e.g. nucleic acids, carbohydrates, lipids) by interaction with immobilised, e.g. 6×His-tagged proteins, e.g. within the scope of cell measurement proteomics projects, active substance screening programs;
- isolation of whole organisms (cells, phages) which express specific biomolecules (e.g. proteins) on their surface, via their specific interaction with immobilised interaction partners, e.g. 6×His-tagged proteins immobilised on Ni-NTA matrix (affinity enrichment, expression cloning, panning).
- gene expression analysis at the protein level (protein expression profiling).

The present invention further relates to the use of an apparatus comprising:

- means for holding a multi-chamber unit in a first position,
- means for holding a multi-chamber unit in a second position,
- means for applying a pressure differential between the inlet end and the outlet end of at least the multichamber unit in the first position, and
- means for adding reagents to individual chambers of at least the multi-chamber unit in the first position, for recovering clear protein-containing solutions from biological samples.

In the first position a multi-chamber filtration unit for receiving protein-containing solutions which contain insoluble ingredients is prepared. In the second position a multichamber collecting unit for collecting the clear protein-containing solutions is provided. Particularly if it is intended subsequently to recover peptides and/or polypeptides from the protein-containing solutions, the multichamber unit in the second position is generally another multichamber filtration unit or a multi-chamber chromatography unit.

The means for applying a pressure differential between the inlet end and the outlet end of at least the multichamber unit in the first position consist of an apparatus for producing an overpressure at the inlet end and/or an underpressure at the outlet end. These means preferably comprise a vacuum device at the outlet end. The multichamber unit in the first position closes off the inlet end from the outlet end to form a substantially tight seal in order to enable a pressure differential to be produced. The pressure difference may be produced between the inlet end and the outlet end of the multichamber unit in the first position or between the inlet end of the multichamber unit in the first position and the outlet end of the multi-chamber unit in the second position. The apparatus optionally also comprises means for applying a pressure differential between the inlet end and outlet end of the multichamber unit in the second position.

The means for adding reagents comprise in particular pipetting means, preferably multiple pipetting means for adding lysing solutions, washing buffers etc to the individual chambers.

The multi-chamber units in the first and second positions are generally aligned so that the outlets of the chambers of one unit in the first position are in alignment with the inlet of the chambers of a unit in the second position. This ensures easy transfer of solutions from the chambers of the unit in the first position after passing through the filtering means into the chambers of the unit in the second position.

When the apparatus is used to recover peptides and/or polypeptides, in the first position a multi-chamber filtration unit is provided and in the second position a multi-chamber collecting unit, preferably another filtration unit or chromatography unit is provided. After the lysates have been filtered through the multichamber filtration unit the clear solutions are contained in the chambers of the second multichamber filtration unit or chromatography unit and are amenable to further manipulation. For another filtration or chromatography step, at least in the specific embodiments, additional vacuum pumps are required at the outlet end of the multi-chamber unit in the second position. By removing the multi-chamber unit in the first position and moving the multi-chamber unit from the second position into the first position this requirement is done away with. In one particular embodiment the apparatus thus comprises:

means for removing a multi-chamber unit from the first position, means for transferring a multi-chamber unit from the second to the first position and means for transferring a multi-chamber unit into the second position.

The additional third multi-chamber unit placed in the second position is a multi-chamber filtration unit, chromatography unit or collecting unit, depending on the particular sequence of processes envisaged.

The apparatus optionally comprises a multi-chamber transfer unit for the contamination-free transfer of solutions from a multi-chamber unit into a subsequent multi-chamber unit and preferably a multi-chamber drainage unit for removing solutions which are to be discarded, which are taken to a waste collection tank. The drainage unit is preferably coupled to a vacuum device. The drainage unit and/or transfer unit is preferably movably mounted, the inlet openings of the drainage unit being operatively connected to the outlets of a multi-chamber unit to form a substantially tight seal in an operative position while in a non-operative position a passage is opened up for liquids to pass from the outlet end of a multi-chamber unit to the inlet end of a subsequent multi-chamber unit. Accordingly, the apparatus preferably also comprises means for releasably attaching the multi-chamber drainage unit to the outlet end of a multi-chamber unit in the first and/or second position. Optionally, the connection between the outlet end of the multi-chamber unit and the multi-chamber drainage unit may be provided via the multi-chamber transfer unit. Similarly, means may be provided for moving a multi-chamber transfer unit in the first and/or second position between an operative and a non-operative position.

The device may further comprise means for analysing cell contents, such as electrophoresis equipment and/or spectrometers, as well as suitable control instruments and/or means for taking aliquots from a multi-chamber collecting unit and/or for supplying an analytical agent. The apparatus also preferably comprises software allowing control of at least one step of the process. Preferably, the software can control the temperature, the duration of the steps of the process and the means for producing the pressure difference.

The invention further relates to a reagent kit for recovering protein-containing solutions from biological samples in a high throughput process, comprising at least one multi-chamber filtration unit and antifoams and/or at least one multi-chamber transfer unit. The reagent kit according to the invention optionally contains one or more other multi-chamber units, for example a multi-chamber receiving unit.

In a particular embodiment the reagent kit according to the invention further comprises at least one reagent for cell lysates, preferably for cell lysates under protein-solubilising conditions. The reagent kit optionally also comprises one or more reagents for solubilising proteins and/or peptides.

The reagent kit according to the invention comprises chromatographic material in a preferred embodiment. The chromatographic material may be, for example, material of the suspension type, contained in a separate container and dispensed into the individual chambers of a multi-chamber unit by the user as required. Preferably, the chromatographic material is already in dispensed form, i.e. in the form of a multi-chamber chromatography unit. Chromatographic materials of the membrane type are preferably also present in the form of a multi-chamber chromatography unit for direct use in the process according to the invention.

The reagent kit according to the invention also optionally contains conventional reagents such as equilibration and washing buffers and/or equipment needed to perform the steps of the process, such as pipette tips, for example.

The invention is explained more fully by means of the Figures and Examples which follow.

EXAMPLES

1. Automated Purification of 6×His Fusion Proteins by Metal Affinity Chromatography (Matrix Suspension) in a 96-Chamber Format.

This example shows the automated purification of proteins from cell lysates of *Escherichia coli* (*E. coli*) by means of dispensed chromatographic material (Ni-NTA superflow) under native conditions in a 96-chamber format using vacuum technology.

*E. coli* DH5α cells which express the protein chloramphenicol acetyl transferase as a fusion protein with an affinity label consisting of 6 times the amino acid histidine (6×His-CAT) were cultured in culture volumes of 5 ml in 24-chamber blocks (each chamber having a capacity of 10 ml; total of 96 batches) and after culturing has ended, sedimented by centrifugation and the supernatant culture medium was eliminated. All the subsequent steps were carried out using a laboratory robot (BioRobot 9600, Qiagen). First, the cell sediments were taken up in 1 ml of lysing buffer (50 mM NaH$_2$PO$_4$, pH 8.0, 300 mM NaCl, 20 mM imidazole, 200 µg/ml of lysozyme) to open up the cells and shaken to ensure total break-up. In the meantime Ni-NTA Superflow Affinity Matrix (Qiagen) was resuspended and dispensed into the chambers of another 96 chamber filtration unit (50 µl bed volume per chamber), the matrix was equilibrated and this unit (Ni-NTA plate) was positioned in the bottom position of a vacuum chamber. Precisely above the Ni-NTA plate a filtration unit (e.g. TurboFilter 96, Qiagen) was placed in the top position. The lysates were transferred into the TurboFilter 96 filtration unit; then the lysates were overlaid with 100 µl of ethanol (100% p.a.) and a vacuum was applied. Then the TurboFilter 96 unit was removed, the Ni-NTA plate containing the clear lysates was transferred into the top position of the vacuum chamber and the drainage block was placed in the bottom position. By applying a vacuum the clear lysates were sucked through the bed of the chromatography matrix; during this process the 6xHis-tagged proteins were bound to the matrix. By twice adding 1 ml of buffer (50 mM NaH$_2$PO$_4$, pH 8.0, 300 mM NaCl, 20 mM imidazole) and subsequently applying a vacuum, the batches were washed. The drainage block in the lower position of the vacuum chamber was replaced by a microtitre plate. 300 µl of elution buffer (50 mM NaH$_2$PO$_4$, pH 8.0, 300 mM NaCl, 250 mM imidazole) was added to the individual chambers and the 6xHis-tagged proteins were eluted into the chambers of the microtitre plate by the application of a vacuum.

The protein concentration in the elution fractions of chambers 1 to 56 was determined by Bradford analysis (Table 1). The yield of 6xHis-CAT is between 21 and 240 µl per chamber (on single elution with 300 µl). The purified proteins are apparently homogeneous according to SDS polyacrylamide gel electrophoresis of 5 µl of each elution fraction and subsequent staining of the protein bands with Coomassie Brilliant Blue (SDS-PAGE analysis; not shown).

TABLE 1

Automated purification of 6xHis-fusion proteins by metal affinity chromatography (matrix suspension) in a 96 chamber format.

| Well | Yield (µg) |
| --- | --- |
| A1 | 64 |
| A2 | 108 |
| A3 | 64 |
| A4 | 240 |
| A5 | 67 |
| A6 | 94 |
| A7 | 77 |
| A8 | 65 |
| A9 | 89 |
| A10 | 102 |
| A11 | 61 |
| A12 | 56 |
| B1 | 64 |
| B2 | 111 |
| B3 | 86 |
| B4 | 52 |
| B5 | 90 |
| B6 | 59 |
| B7 | 80 |
| B8 | 111 |
| B9 | 178 |
| B10 | 91 |
| B11 | 104 |
| B12 | 178 |
| C1 | 237 |
| C2 | 88 |
| C3 | 84 |
| C4 | 74 |
| C5 | 72 |
| C6 | 91 |
| C7 | 191 |
| C8 | 109 |
| C9 | 70 |
| C10 | 91 |
| C11 | 90 |
| C12 | 60 |
| D1 | 84 |
| D2 | 71 |
| D3 | 88 |
| D4 | 93 |
| D5 | 81 |
| D6 | 21 |
| D7 | 98 |
| D8 | 40 |
| D9 | 77 |
| D10 | 62 |
| D11 | 44 |
| D12 | 135 |
| E1 | 54 |
| E2 | 76 |
| E3 | 71 |
| E4 | 87 |
| E5 | 58 |
| E6 | 91 |
| E7 | 84 |
| E8 | 84 |

Yield (µg) average: 93
Standard deviation: 42

2. Automated Purification of 6xHis Fusion Proteins by Metal Affinity Chromatography (Membrane) in a 96 Chamber Format This example illustrates the automated purification of proteins from cell lysates of *Escherichia coli* through an affinity membrane (containing Ni-NTA silica particles polymerised therein) under native conditions in a 96 chamber format using vacuum technology.

The equipment and method for the experiment forming the basis of Example 2 are the same as in Example 1 except that a 96 chamber plate was used in which the affinity membrane for the binding of the 6xHis fusion proteins had previously been incorporated. Ni-NTA silica particles (QIAGEN) were incorporated in the membrane.

The protein concentrations in the elution fractions of chambers 1 to 62 were determined by Bradford Analysis (Table 2). The yield of 6xHis CAT is between 50 and 250 µg per chamber (after single elution with 300 µl). The purified proteins are apparently homogeneous according to SDS polyacrylamide gel electrophoresis of 5 µl of each elution fraction and subsequent staining of the protein bands with Coomassie-Brilliant Blue (SDS-PAGE Analysis; not shown).

TABLE 2

Automated purification of 6xHis fusion proteins by metal affinity chromatography (membrane) in a 96 chamber format.

| Well | Yield (µg) |
| --- | --- |
| A1 | 250 |
| A2 | 169 |
| A3 | 174 |
| A4 | 149 |
| A5 | 179 |
| A6 | 93 |

TABLE 2-continued

Automated purification of 6xHis fusion proteins by metal affinity chromatography (membrane) in a 96 chamber format.

| Well | Yield ($\mu$g) |
|---|---|
| A7 | 152 |
| A8 | 131 |
| A9 | 171 |
| A10 | 156 |
| A11 | 123 |
| A12 | 106 |
| B1 | 225 |
| B2 | 176 |
| B3 | 148 |
| B4 | 153 |
| B5 | 148 |
| B6 | 143 |
| B7 | 129 |
| B8 | 137 |
| B9 | 126 |
| B10 | 130 |
| B11 | 246 |
| B12 | 102 |
| C1 | 129 |
| C2 | 190 |
| C3 | 202 |
| C4 | 151 |
| C5 | 196 |
| C6 | 134 |
| C7 | 145 |
| C8 | 128 |
| C9 | 147 |
| C10 | 184 |
| C11 | 137 |
| C12 | 103 |
| D1 | 91 |
| D2 | 117 |
| D3 | 168 |
| D4 | 90 |
| D5 | 73 |
| D6 | 131 |
| D7 | 137 |
| D8 | 117 |
| D9 | 160 |
| D10 | 113 |
| D11 | 145 |
| D12 | 93 |
| E1 | 158 |
| E2 | 127 |
| E3 | 166 |
| E4 | 49 |
| E5 | 121 |
| E6 | 59 |
| E7 | 170 |
| E8 | 98 |
| E9 | 145 |
| E10 | 147 |
| E11 | 130 |
| E12 | 129 |
| F1 | 172 |
| F2 | 131 |

Yield ($\mu$g) average: 142
Standard deviation: 39

3. Automated Purification of Chloramphenicol-Acetyl-Transferase (CAT) by Anion Exchange Chromatography (Matrix Suspension) in a 96 Chamber Format.

This Example illustrates the automated purification of the protein CAT from cell lysates of *Escherichia coli* through dispensed anion exchange chromatographic material (Q-Sepharose Fast Flow) under native conditions in a 96 chamber format using vacuum technology.

The equipment and procedures for the experiment forming the basis for Example 3 correspond to those used for Example 1 with one alteration. The fact that Chloramphenicol-Acetyl-Transferase (CAT) can be purified by anion exchange chromatography was exploited. In the test described here, a 96 chamber plate with a dispensed suspension of the Q-Spharose Fast Flow Anion Exchange matrix (Amersham Pharmacia Biotech) was used to bind the recombinant protein (lysing buffer: 50 mm Tris HCl, 25 mM NaCl, 200 $\mu$g/ml lysozyme, pH 7.0; binding buffer/washing buffer: 50 mM Tris HCl, 25 mM NaCl, pH 7.0; elution buffer: 50 mM Tris HCl, 500 mM NaCl, pH 7.0).

Figure 1:
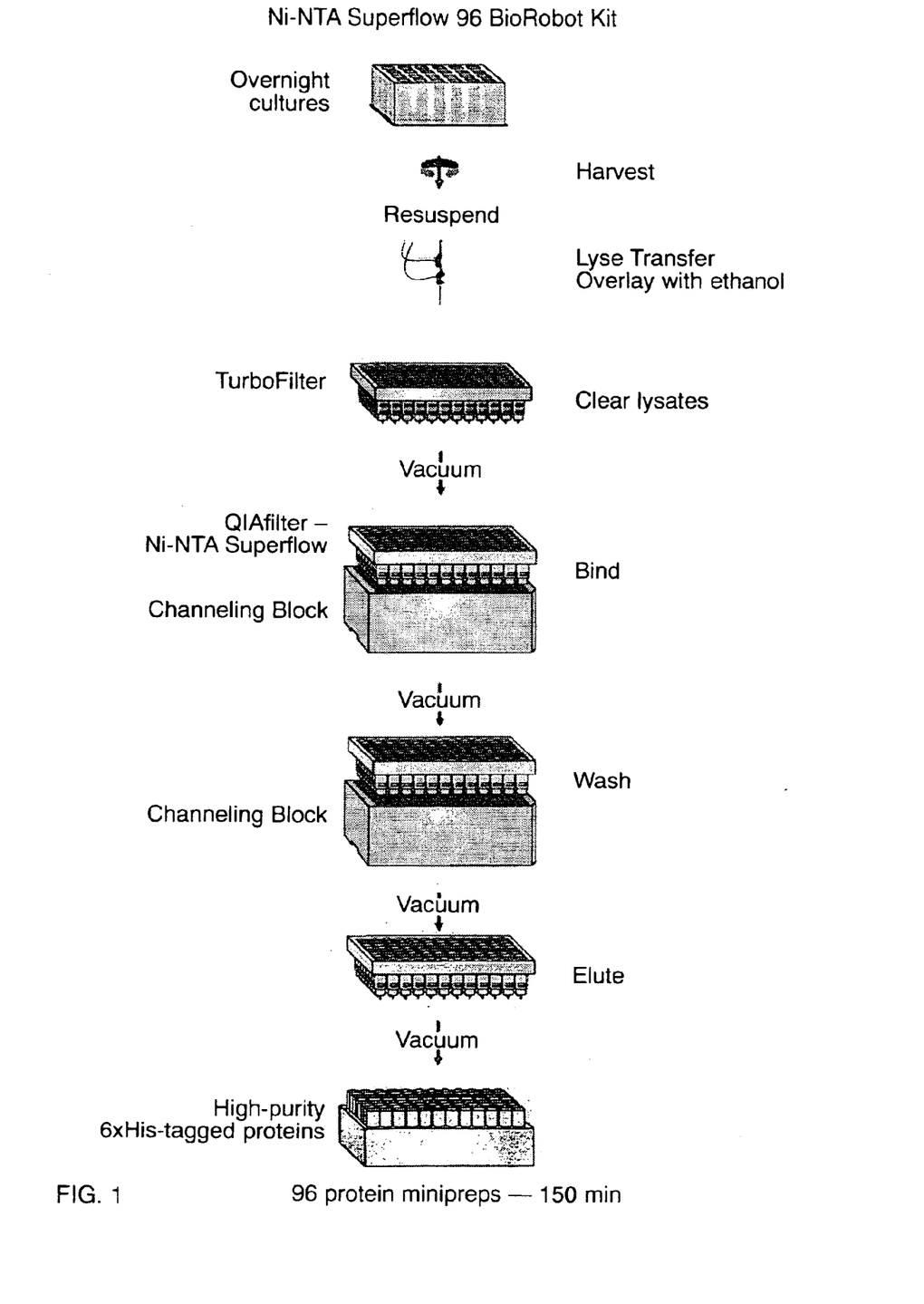
FIG. 1 shows an embodiment of the process according to the invention.
Figure 2:
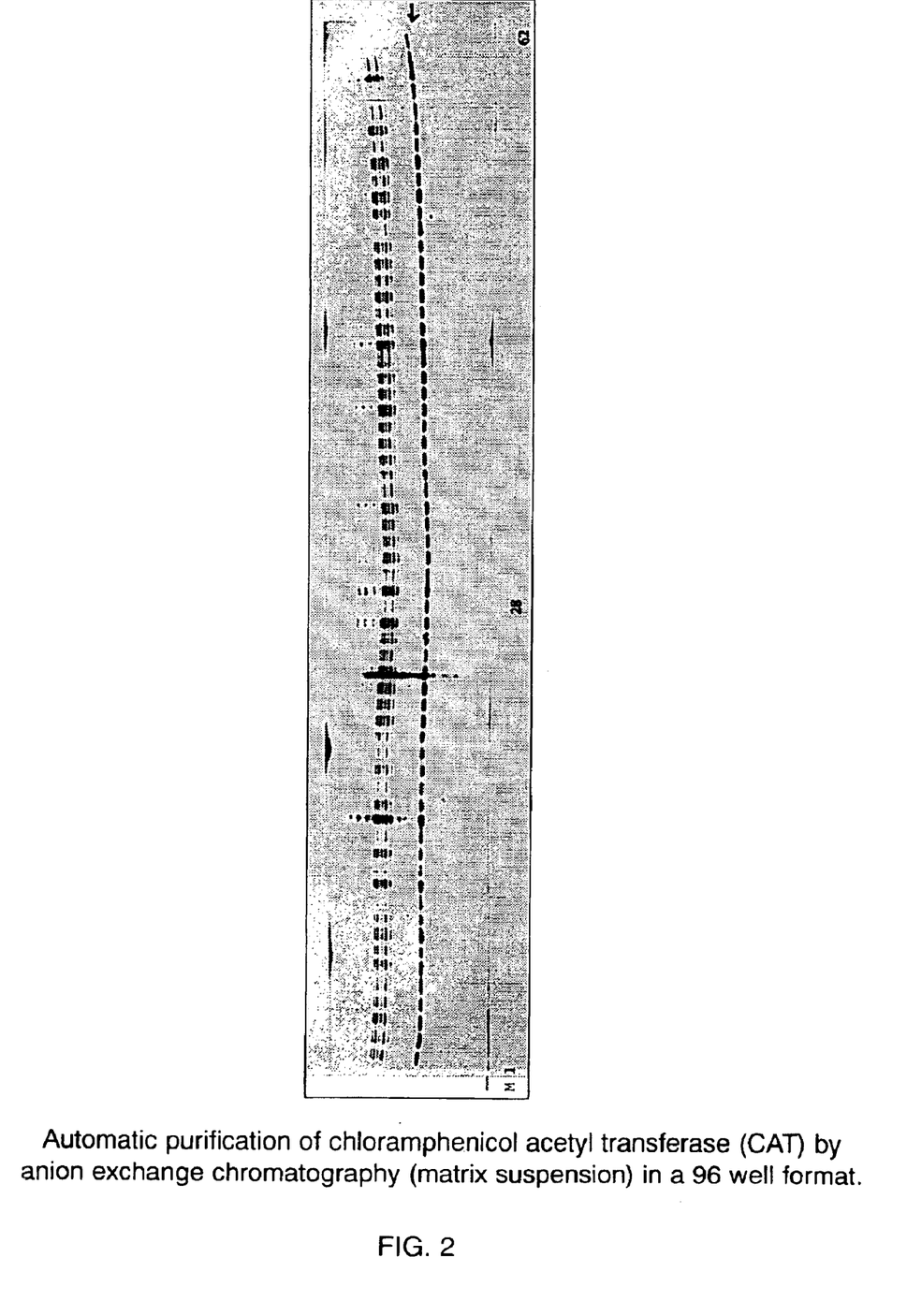
FIG. 2 shows an SDS polyacrylamide gel of purified CAT by anion exchange chromatography according to Example 3 using a matrix suspension.

The protein concentrations in the elution fractions of chambers 1 to 62 were determined by Bradford Analysis (Table 3). 5 $\mu$l of each fraction were charged onto an SDS polyacrylamide gel (SDS-PAGE 15%). The protein bands in the gel were made visible by staining with Coomassie-Brilliant-Blue (FIG. 2). CAT could then be concentrated to a purity of about 40%. The yield of CAT is between 40 and 120 $\mu$g per chamber (after a single elution with 200 $\mu$l).

TABLE 3

Automated purification of Chloramphenicol-Acetyl-Transferase by Anion Exchange Chromatography (matrix suspension) in a 96-chamber format.

| Well | Yield ($\mu$g) |
|---|---|
| A1 | 152 |
| A2 | 125 |
| A3 | 116 |
| A4 | 151 |
| A5 | 206 |
| A6 | 127 |
| A7 | 213 |
| A8 | 194 |
| A9 | 215 |
| A10 | 121 |
| A11 | 107 |
| A12 | 162 |
| B1 | 156 |
| B2 | 110 |
| B3 | 134 |
| B4 | 162 |
| B5 | 213 |
| B6 | 209 |
| B7 | 161 |
| B8 | 133 |
| B9 | 135 |
| B10 | 176 |
| B11 | 147 |
| B12 | 108 |
| C1 | 98 |
| C2 | 158 |
| C3 | 152 |
| C4 | 266 |
| C5 | 157 |
| C6 | 222 |
| C7 | 138 |
| C8 | 163 |
| C9 | 125 |
| C10 | 166 |
| C11 | 159 |
| C12 | 108 |
| D1 | 149 |
| D2 | 146 |
| D3 | 141 |
| D4 | 132 |
| D5 | 117 |
| D6 | 240 |
| D7 | 192 |
| D8 | 209 |
| D9 | 147 |
| D10 | 206 |
| D11 | 153 |
| D12 | 112 |
| E1 | 118 |
| E2 | 169 |
| E3 | 165 |
| E4 | 301 |
| E5 | 158 |
| E6 | 228 |

TABLE 3-continued

Automated purification of Chloramphenicol-Acetyl-Transferase by Anion Exchange Chromatography (matrix suspension) in a 96-chamber format.

| Well | Yield (μg) |
| --- | --- |
| E7 | 301 |
| E8 | 191 |
| E9 | 226 |
| E10 | 149 |
| E11 | 204 |
| E12 | 110 |
| F1 | 172 |
| F2 | 131 |

Yield (μg) average: 165
Standard deviation: 46

4. Automated Purification of Eukaryotically Expressed 6xHis Fusion Proteins by Metal Affinity Chromatography (Matrix Suspension) in a 96 Chamber Format.

This example describes the purification of 6xHis fusion proteins from cell lysates of the yeast *Saccharomyces cerevisiae* through dispensed chromatographic material (Ni-NTA superflow) under native conditions in a 96 chamber format using vacuum technology.

The equipment and procedure for the experiment on which Example 4 is based correspond to those used in Example 1 except that in the experiment described here the 6xHis-tagged protein FBA1-aldolase expressed in eukaryotic *Saccharomyces cerevisiae* cells was purified. To do this the lysing conditions were altered as follows: the cells cultured in 5 ml of culture medium in 24 chamber blocks were resuspended in lysing buffer (20 mm $KH_2PO_4$/$K_2HPO_4$, pH 7.4; 1.2 M sorbitol; 1 mg/ml zymolyase) and shaken for 45 minutes to assist the formation of spheroplasts. Then protease inhibitor, 300 mm NaCl and 0.4% (v/v) of Triton x-100 were added to lyse the spheroplasts and the lysing mixtures were transferred to a filtration unit (e.g. TurboFilter 96, QIAGEN) for clarification. All the subsequent steps were carried out as described in Example 1.

The protein concentrations in the elution fractions were determined by Bradford Analysis (Table 4). The yield of 6xHis-FBA1 aldolase was between 10 and 25 μg per chamber. The purified proteins are apparently homogenous according to SDS-PAGE analysis (not shown).

TABLE 4

Automated purification of eukaryotically expressed 6xHis fusion proteins by metal affinity chromatography (matrix suspension) in a 96 chamber format.

| Well | Yield (μg) |
| --- | --- |
| A1 | 15 |
| A2 | 16 |
| A3 | 11 |
| A4 | 21 |
| A5 | 13 |
| A6 | 19 |
| B1 | 16 |
| B2 | 24 |
| B3 | 8 |
| B4 | 9 |
| B5 | 17 |
| B6 | 15 |
| C1 | 16 |
| C2 | 10 |
| C3 | 16 |
| C4 | 12 |
| C5 | 11 |
| C6 | 17 |
| D1 | 18 |
| D2 | 14 |
| D3 | 17 |
| D4 | 16 |
| D5 | 18 |
| D6 | 15 |
| E1 | 16 |
| E2 | 16 |
| E3 | 12 |
| E4 | 15 |
| E5 | 17 |
| E5 | 17 |
| F1 | 15 |
| F2 | 16 |
| F3 | 22 |
| F4 | 10 |
| F5 | 19 |
| F6 | 14 |
| G1 | 12 |
| D2 | 12 |
| G2 | 8 |
| D3 | 21 |
| G3 | 15 |
| D4 | 18 |
| H1 | 11 |
| H2 | 16 |
| H3 | 10 |
| H4 | 16 |
| H5 | 13 |
| H6 | 19 |

Yield (μg) average: 15
Standard deviation: 4

5. Automated Purification of 6xHis-Tagged Fusion Proteins by Metal Affinity Chromatography (Matrix Suspension) in a 96 Chamber Format Under Denaturing Conditions.

This Example shows the automated purification of proteins from cell lysates of *Escherichia coli* through dispensed chromatographic material (Ni-NTA Superflow) under denaturing conditions in a 96-chamber format using vacuum technology.

*E. coli* M15/pREP4 cells which express thioredoxin as a fusion protein with an affinity labelling (6xHis) consisting of 6 times the amino acid histidine were cultured in culture volumes of 5 ml in 24-chamber blocks (capacity of each chamber 10 ml; total of 96 batches) and after culturing has ended, sedimented by centrifugation; supernatant culture medium was removed. All subsequent steps were carried out using a laboratory robot (BioRobot 9600, QIAGEN). First, the cell sediments were taken up in 1 ml of lysing buffer (8 M urea, 100 mM $NaH_2PO_4$, 10 mM Tris HCl, pH 8.0) to open up the cells and shaken for 30 minutes to assist total break-up. Meanwhile Ni-NTA Superflow affinity matrix was resuspended and dispensed into the chambers of another 96 chamber unit (50 μl of bed volume per chamber), the matrix was equilibrated and this unit (Ni-NTA plate) was placed in the lower position of a vacuum chamber. A filtration unit (e.g. TurboFilter 96, QIAGEN) was positioned in the top position precisely above the Ni-NTA plate. The lysates were transferred into the TurboFilter 96 filtration unit; then the lysates were overlaid with 100 μl of ethanol (p.a.) and a vacuum was applied. After filtration had ended the Turbo-Filter 96 unit was removed, the Ni-NTA plate containing the clear lysates was transferred into the top position of the vacuum chamber and the drainage block was placed in the lower position. By applying a vacuum, the clear lysates were sucked through the bed of the chromatographic matrix; during this process the 6×His-tagged proteins were bound to the matrix. By twice adding 1 ml of washing buffer 1 (8 M urea, 100 mM $NaH_2PO_4$, 10 mM Tris HCl, pH 8.0) and once adding washing buffer 2 (8M urea, 100 mM $NaH_2PO_4$, 10 mM Tris HCl, pH 6.3) and then applying a vacuum, the batches were washed. The drainage block in the bottom position of the vacuum chamber was replaced by a microtitre plate. 300 µl of elution buffer (8 M urea, 100 mM $NaH_2PO_4$, 10 mM Tris HCl, pH 4.5) were added to the individual chambers and the 6×His-tagged proteins were eluted into the chambers of the microtitre plate by the application of a vacuum.

The protein concentrations in the elution fractions of chambers 1 to 54 were determined by Bradford analysis (Table 5). The yield of 6×His-labelled protein was between 86 and 252 µg per well. The purified proteins are apparently homogenous according to SDS-PAGE analysis (not shown).

TABLE 5

| Well | Yield (µg) |
|---|---|
| A1 | 110 |
| A2 | 131 |
| A3 | 185 |
| A4 | 198 |
| A5 | 100 |
| A6 | 114 |
| A7 | 192 |
| A8 | 156 |
| A9 | 248 |
| A10 | 180 |
| A11 | 161 |
| A12 | 160 |
| B1 | 129 |
| B2 | 130 |
| B3 | 143 |
| B4 | 197 |
| B5 | 142 |
| B6 | 221 |
| B7 | 203 |
| B8 | 157 |
| B9 | 182 |
| B10 | 153 |
| B11 | 167 |
| B12 | 156 |
| C1 | 131 |
| C2 | 118 |
| C3 | 147 |
| C4 | 132 |
| C5 | 147 |
| C6 | 118 |
| C7 | 155 |
| C8 | 180 |
| C9 | 171 |
| C10 | 186 |
| C11 | 152 |
| C12 | 145 |
| D1 | 112 |
| D2 | 174 |
| D3 | 152 |
| D4 | 156 |
| D5 | 111 |
| D6 | 97 |
| D7 | 216 |
| D8 | 220 |
| D9 | 171 |
| D10 | 155 |
| D11 | 151 |
| D12 | 141 |
| E1 | 104 |
| E2 | 153 |
| E3 | 140 |
| E4 | 137 |

TABLE 5-continued

| Well | Yield (µg) |
|---|---|
| E5 | 86 |
| E6 | 183 |
| E7 | 252 |
| E8 | 174 |
| E9 | 115 |
| E10 | 196 |
| E11 | 196 |
| E12 | 143 |
| F1 | 150 |
| F2 | 159 |

Yield (µg) average: 156
Standard deviation: 36

6. Purification of Different 6×His Fusion Proteins, without any Cross Contamination, by Metal Affinity Chromatography in a 96 Chamber Format This Example describes the automated purification of proteins from cell lysates of *Escherichia coli* through dispensed chromatographic material (Ni-NTA Superflow) under denaturing conditions in a 96 chamber format using vacuum technology, including measures to prevent cross contamination, compared with purification carried out without these measures.

The equipment and procedure for the experiment on which Example 6 is based correspond to those described for Example 5 except that different clones expressing 6×His fusion proteins were cultivated in 5 ml of medium and worked up in parallel. The measures taken to prevent cross contamination (overlaying with ethanol, use of a drainage block) are described in Example 4.

Figure 3A:
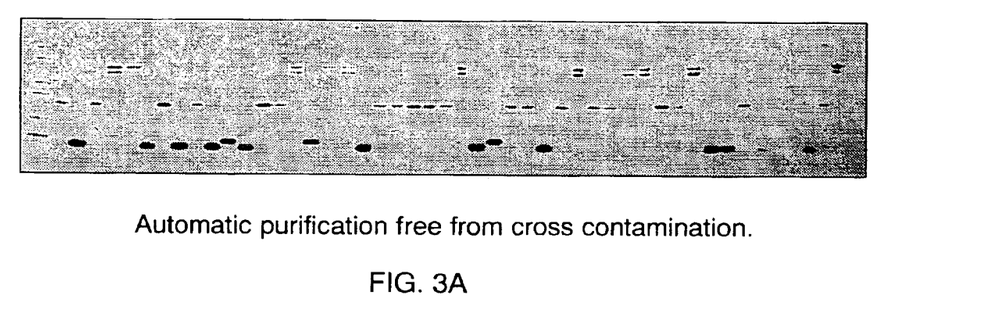
FIG. 3a shows an SDS polyacrylamide gel of different 6×His fusion proteins purified by metal chelate affinity chromatography using the process according to the invention as described in Example 6.
Figure 3B:
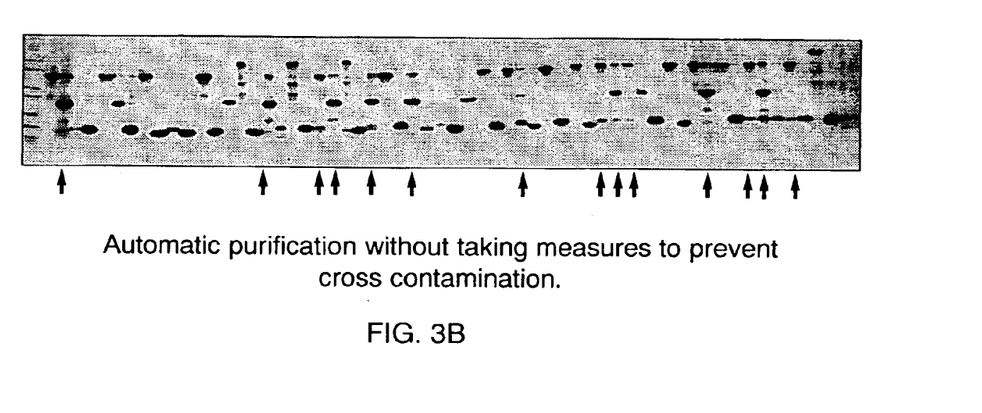
FIG. 3b shows an SDS polyacrylamide gel of different 6×His fusion proteins purified by metal chelate affinity chromatography by a conventional method as described in Example 6 by way of a comparison.

5 µl aliquots of the elution fractions specified were heated for 4 minutes at 95° C. and analysed by SDS-PAGE and subsequent Coomassie staining of the protein bands (FIG. 3). The pattern of bands of the elution fractions purified using the process according to the invention (FIG. 3a) shows that only one band corresponding to one of the 6×His fusion proteins appears in the fractions and therefore cross contamination can be prevented by this method. By contrast, in the control experiment, in some cases several bands corresponding to a 6×His fusion protein can be identified (FIG. 3b, bands indicated by ↑).

What is claimed is:

1. A process for recovering clear solutions containing cell contents from biological samples in a high throughput process, comprising the steps of:
    (a) preparing a plurality of protein-containing solutions which contain insoluble ingredients in separate chambers of a multi-chamber filtration unit,
    (b) removing insoluble ingredients by filtering the solutions through the multi-chamber filtration unit with the application of a pressure differential, cross contamination of adjacent chambers being prevented by the addition of an anti foam to said protein-containing solutions and, optionally, by the use of a transfer unit between the outlet end of the multi-chamber filtration unit and the inlet end of the collecting containers, and
    (c) collecting the individual filtrates separately in collecting containers.

2. The process according to claim 1, wherein the antifoam is selected from primary, secondary or tertiary $C_{1-6}$ alcohols, silicone antifoams, nonsilicone antifoams, plant-based antifoams, long-chained alkanes, polypropylene glycols, polyethylene glycols and mixtures thereof.

3. The process according to claim 1, wherein the solutions containing protein according to (a) are crude cell lysates.

4. The process according to claim 3, wherein the cell lysis is carried out in the separate chambers of the multi-chamber filtration unit.

5. The process according to claim 1, wherein the pore size of the filters in the multi-chamber filtration unit decreases in the direction of flow of the filtrate through the filter.

6. The process according to claim 1, further comprising recovering cell contents from filtrates according to (c).

7. The process according to claim 6, comprising at least one further filtration step.

8. The process according to claim 7, comprising at least one chromatographic separation step and/or precipitation step.

9. The process according to claim 8, comprising a chromatographic separation step using an ion exchange matrix or an affinity matrix.

10. The process according to claim 9, wherein the affinity matrix is a metal chelate affinity matrix.

11. The process according to claim 10, wherein the metal chelate affinity matrix is an Ni-NTA matrix.

12. The process according to one of claims 9 to 11, wherein the matrix is a suspension.

13. The process according to claim 1, further comprising at least one washing step.

14. The process according to claim 1, wherein the liquids are separated by the application of a pressure differential.

15. The process according to claim 14, wherein liquids to be discarded are eliminated using a drainage unit.

16. The process according to claim 1, further comprising at least one step of analysing the cell contents.

17. The process according to claim 1, wherein the cell contents are collected in a multi-chamber unit.

18. The process according to claim 17, wherein the cell contents are selected from peptides, polypeptides, nucleic acids and metabolites.

19. A method for recovering clear protein-containing solutions from biological samples comprising:
 1) introducing a biological sample to an apparatus comprising:
  (i) a multi-chamber unit;
  (ii) means for holding the multi-chamber unit in a first position,
  (iii) means for holding the multi-chamber unit in a second position,
  (iv) means for applying a pressure differential between the inlet end and the outlet end of at least the multi-chamber unit in the first position, and
  (v) means for adding reagents to individual chambers of at least the multi-chamber unit in the first position,
 2) providing antifoam to individual chambers of said multi-chamber unit to prevent cross-contamination between individual chambers during filtration; and
 3) recovering clear protein-containing solutions from said biological sample.

20. The method according to claim 19, wherein the multi-chamber units are aligned so that the outlets of the chambers of a unit in the first position are in alignment with the inlets of the chambers of a unit in the second position.

21. The method according to claim 19 or 20, wherein the apparatus further comprises:
 (i) means for removing a multi-chamber unit from the first position,
 (ii) means for transferring a multi-chamber unit from the second to the first position, and
 (iii) means for transferring a multi-chamber unit to the second position.

22. The method according to claim 21, wherein the apparatus further comprises a multi-chamber transfer unit.

23. The method according to claim 22, wherein the apparatus further comprises a multi-chamber drainage unit.

24. The method according to claim 23, wherein the apparatus further comprises means for releasably attaching the multi-chamber drainage unit to the outlet end of a multi-chamber unit in the first and/or second position.

25. The method according to claim 24, wherein the apparatus further comprises means for analysing cell contents.

26. The method according to claim 25, wherein the apparatus further comprises software for controlling at least one process step.

27. A kit for obtaining protein-containing solutions from biological samples in a high throughput process while avoiding cross-contamination caused by foaming of the solution during filtration, comprising:
 (a) at least one multi-chamber filtration unit, wherein each unit is comprised of at least 24 individual chambers in an ordered, closely-spaced arrangement, such that cross-contamination may occur at the exit of individual adjacent chambers during filtration,
 (b) an antifoam added to each chamber of said unit,
 (c) at least one multi-chamber transfer unit, and
 (d) optionally, at least one multi-chamber receiving unit.

28. The kit according to claim 27, further comprising at least one reagent for cell lysis.

29. The kit according to claim 27 or 28, further comprising at least one reagent for solubilising proteins and/or peptides.

30. The kit according to claim 27, further comprising chromatographic material.

31. The kit according to claim 30, wherein the chromatographic material is in the form of at least one multi-chamber chromatography unit.

* * * * *